United States Patent [19]

Fenton et al.

[11] Patent Number: 5,980,930
[45] Date of Patent: Nov. 9, 1999

[54] FIBRES

[75] Inventors: John Charles Fenton, Rhymney; Bryan Griffiths, New Tredegar; Peter Michael John Mahoney, Llanarmon, all of United Kingdom

[73] Assignee: Bristol-Myers Squibb Company, New York, N.Y.

[21] Appl. No.: 08/491,963

[22] PCT Filed: Jan. 19, 1994

[86] PCT No.: PCT/GB94/00102

§ 371 Date: Sep. 15, 1995

§ 102(e) Date: Sep. 15, 1995

[87] PCT Pub. No.: WO94/17227

PCT Pub. Date: Aug. 4, 1994

[30] Foreign Application Priority Data

Jan. 20, 1993 [GB] United Kingdom .................... 9301076
Jan. 20, 1993 [GB] United Kingdom .................... 9301087

[51] Int. Cl.⁶ .................................................. A61L 15/00
[52] U.S. Cl. ........................ 424/443; 424/445; 428/288; 428/292; 428/293; 428/300
[58] Field of Search ...................................... 428/224, 234, 428/284, 288, 292, 293, 300, 107; 424/443, 445

[56] References Cited

U.S. PATENT DOCUMENTS

| | | | |
|---|---|---|---|
| 1,814,981 | 7/1931 | Thornley et al. | 260/400 |
| 4,421,583 | 12/1983 | Aldred et al. | 156/167 |
| 4,562,110 | 12/1985 | Tong | 428/284 |
| 5,238,685 | 8/1993 | Wren | 424/445 |
| 5,256,477 | 10/1993 | Mahoney | 428/283 |

FOREIGN PATENT DOCUMENTS

| | | |
|---|---|---|
| 0439339 | 7/1991 | European Pat. Off. . |
| 1231506 | 5/1971 | United Kingdom . |
| 8002300 | 10/1980 | WIPO . |
| 8403705 | 9/1984 | WIPO . |

OTHER PUBLICATIONS

Database WPI, Section Ch, Week 8705, Derwent Publications Ltd., London, Agency of Ind Sci Tech et al., Dec. 19, 1986; AN 87–033299.

*Primary Examiner*—S. Mark Clardy
*Assistant Examiner*—Kathryne E. Shelborne
*Attorney, Agent, or Firm*—John M. Kilcoyne; Theodore R. Furman, Jr.

[57] ABSTRACT

Highly absorbent alginate fibers are described which have use in the manufacture of dressings. The fibers and dressings described are highly swellable while also being soluble, rather than just being soluble. This is a considerable advantage for use in environments where high absorption coupled with biodegradability is desired, for example, in wound dressings such as dressings for ulcers or burns.

18 Claims, 5 Drawing Sheets

Fig. 2 TGA

FIBRES

This application is a 371 of PCTGB94/00102 Jan. 19, 1994,

The present invention relates to improved absorbency alginate fibres, a process for their preparation and their application in the preparation of alginate fabrics and wound dressings.

Alginate fibres have been known for some time as being useful in the preparation of wound dressings. A number of methods for producing conventional alginate fibres are described in the art. The extrusion of alginate solutions into an aqueous solution containing calcium ions to form calcium alginate filaments is known, for example, from British Patent Specifications Nos. 567641, 568177, 571657 and 624987. The replacement of a proportion of the calcium ions in calcium alginate by sodium ions to produce a more soluble fibre is known from British Patent Specification No. 653341.

A fabric prepared from known calcium alginate fibres can typically absorb 3 to 5 times its own weight of water, and this absorbency can be increased by increasing the proportion of sodium ions to calcium ions in the fabric. In this way, fabrics having an absorbency of approximately 20 times their own-weight of water have been produced, for example, Kaltostat (trademark), a haemostatic wound dressing comprising a carded and needle-tacked web of calcium/sodium alginate fibres. Other factors which affect absorbency of alginate fibres are the nature of the source material and staple length.

We have now found that alginate fibres can be produced which are very much more absorbent than conventional alginate fibres. This is a considerable advantage for use in environments where high absorption coupled with biodegradeability is desired, for example in wound dressings such as dressings for ulcers or burns. The high rate of absorption achieved with fibres of this invention is a further advantage, particularly for use in dressings.

The fibres according to the invention may be characterised by reference to their unique thermal properties.

The present invention thus provides an alginate fibre characterised in that a plot of the first order derivative of percentage weight loss of the fibre with temperature against temperature has two maxima in the range of 100 to 400° C.

In general, the two maxima in the plot of the first order derivative of percentage weight loss with temperature against temperature for a fibre according to the invention will fall within the range 200 to 300° C., preferably 220 to 290° C.

Thermogravimetric analysis was performed using a 2950TGA manufactured by TA Instruments, Delaware, U.S.A. Differential scanning calorimetry (DSC) was performed using a DSC7 manufactured by Perkin-Elmer.

Figure 1:
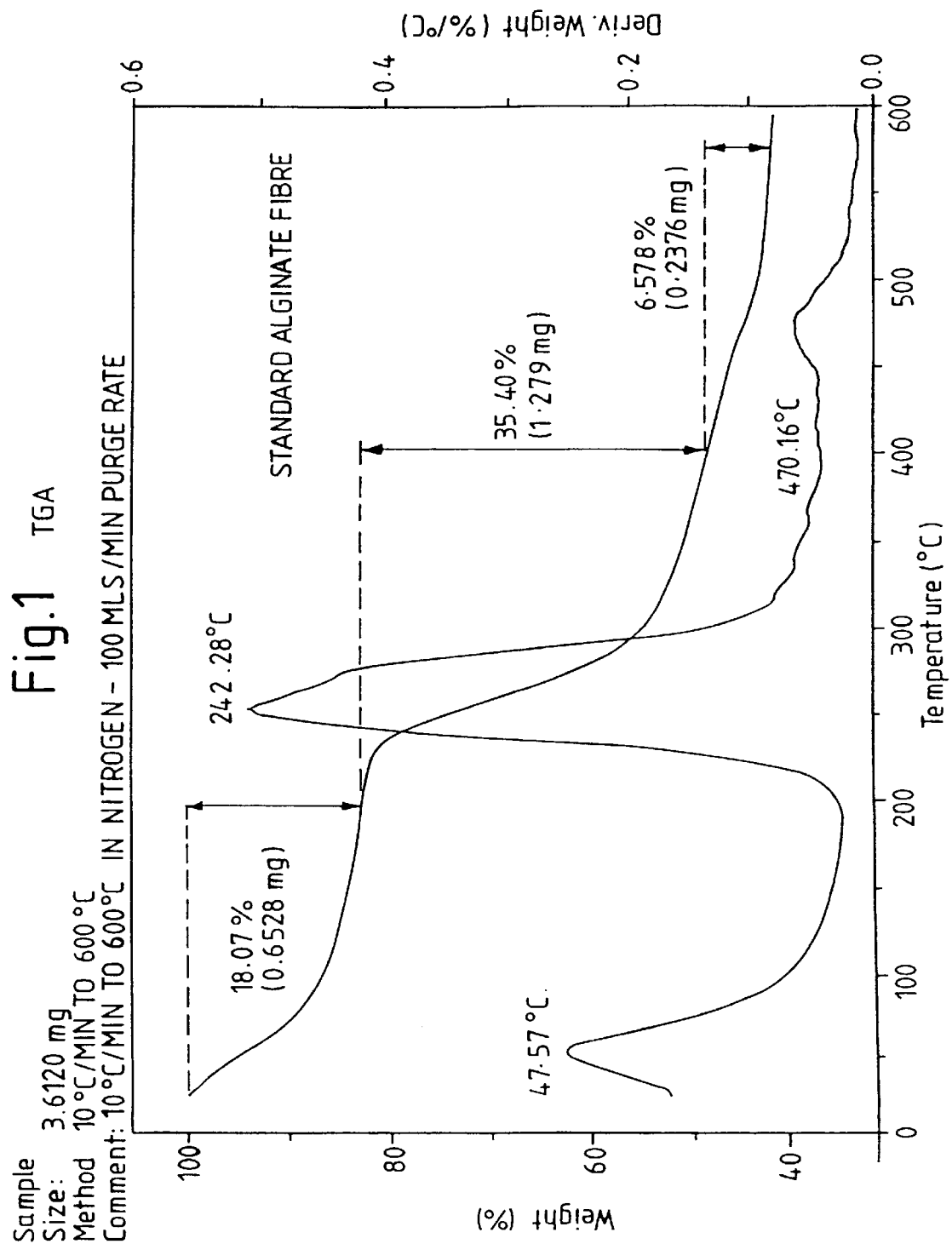
FIG. 1 shows the thermogravimetric analysis (TGA) of an 80:20 calcium:sodium alginate fibre prepared by conventional methods.
Figure 2:
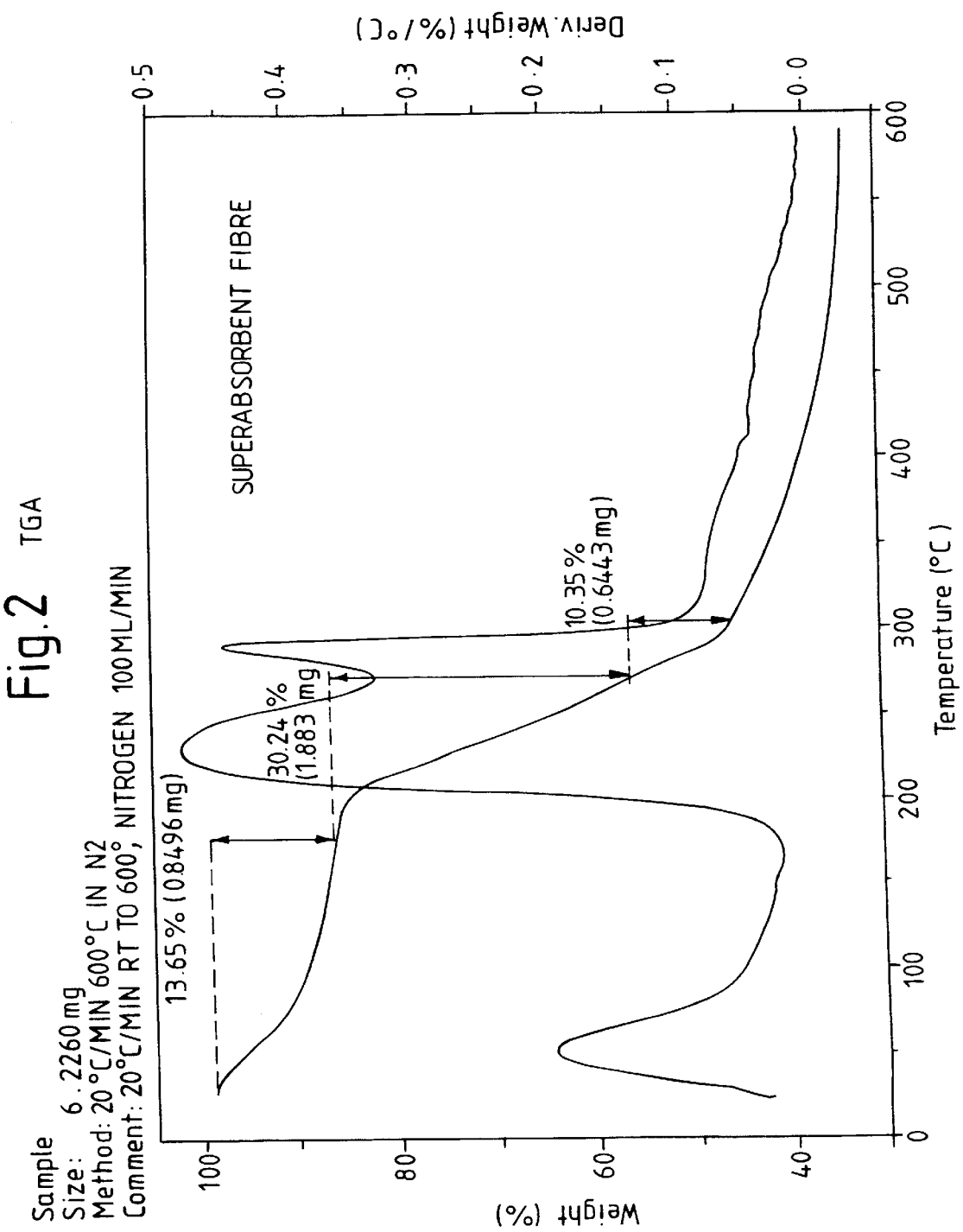
FIG. 2 shows the thermogravimetric analysis (TGA) of a fibre according to the invention, prepared from the same source material as the fibre of FIG. 1.

FIG. 1 shows the percentage weight loss of a conventional alginate fibre with increasing temperature, and the first order derivative of that function. The derivative shows a single maximum at approximately 240° C. In contrast, the first order derivative of percentage weight loss with temperature for a corresponding fibre according to the present invention, shown in FIG. 2, has two peaks, one at a lower temperature than the maximum observed for the conventional fibre (approximately 225° C.), and one at a higher temperature than the maximum observed for the conventional fibre (approximately 280° C.). This "splitting" of the derivative maximum for the conventional fibre of the same composition is characteristic of fibres according to the present invention.

Figure 3:
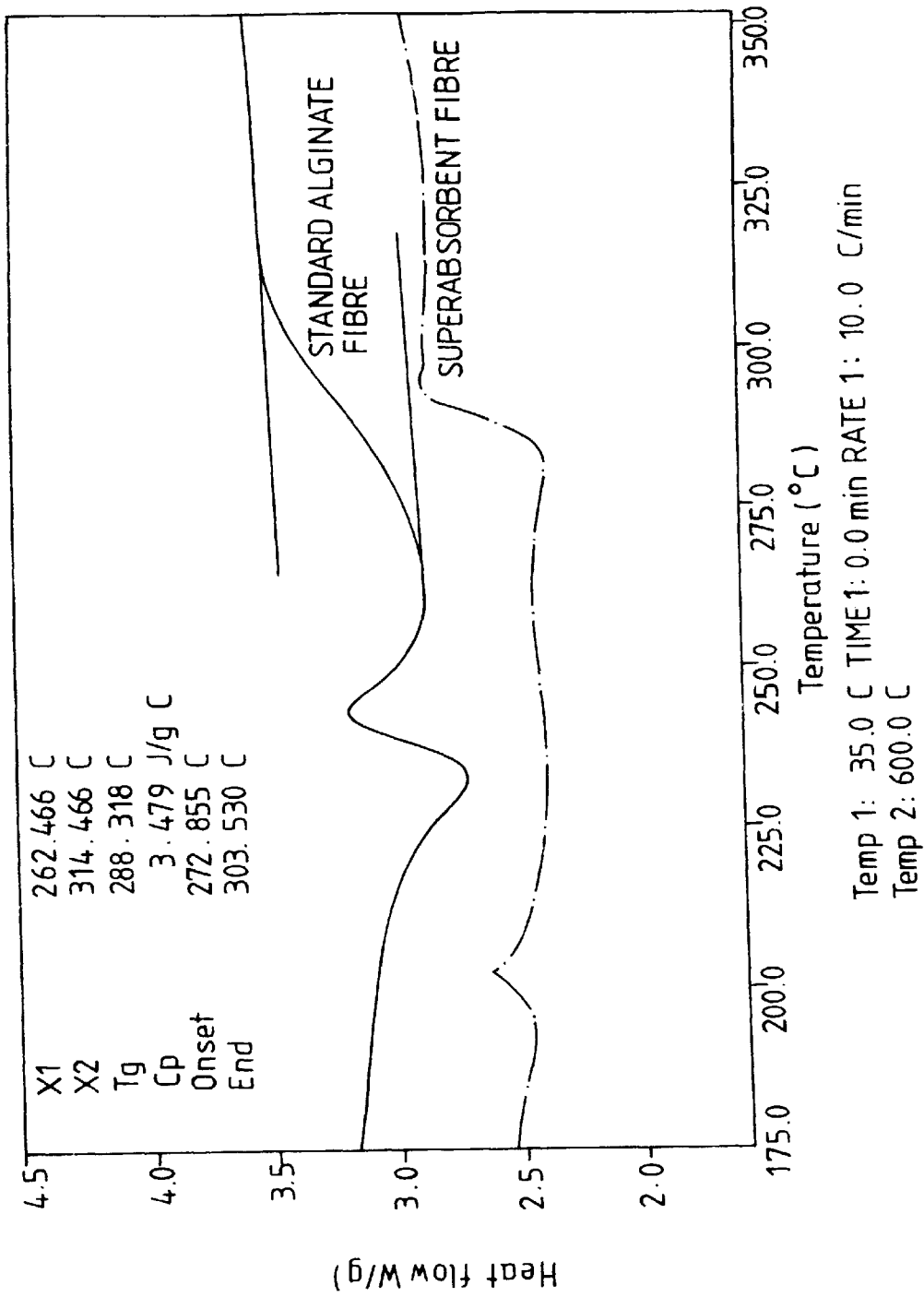
FIG. 3 shows the variation of heat flow with temperature for a conventional 80:20 calcium:sodium alginate fibre and a corresponding fibre in accordance with the present invention.

FIG. 3 also shows differences in the thermal properties of a conventional alginate fibre and a fibre according to the present invention. Heat flow is effectively a measure of enthalpy associated with a transition, reaction or decomposition. The glass transition temperature (Tg) shown in FIG. 3 is the same for both fibres (288° C.). However, it can be seen that the transition for the conventional fibre is broad, occuring over some 50° C., whereas that for the fibre in accordance with the invention is sharp, taking place over less than 20° C.

In a further or alternative aspect, the present invention thus provides an alginate fibre characterised in that its glass transition range is less than 30° C., such as about 26° C.

In a further aspect, there is provided a process for the preparation of the alginate fibres according to the invention, which process comprises the following steps:

(1) treating alginate fibres with a suitable acid so as to produce fibres comprising approximately 90–98%, such as 95%–98%, alginic acid fibres;

(2) treating the alginic acid fibres with a saturated aqueous solution of mono- or divalent cations;

(3) washing the fibres with water until imbibition of water by the fibres has effectively ceased;

(4) treating the fibres with a source of a cation capable of forming a water-soluble alginate salt.

The present invention also provides alginate fibres characterised in that they are prepared according to the above-described process.

The fibres used as starting material in step 1 may be conventional salted alginate fibres (for example sodium, calcium, mixed sodium/calcium fibres produced in conventional manner, for example from 2–10% w/w solutions, for example 4% solution)

Most suitably the alginate fibres for use in step (1) are calcium alginate fibres.

Suitable acids of use in step (1) include acids capable of protonating alginic acid and may include both organic and inorganic acids. Preferably, hydrochloric acid will be used. Preferably the resulting alginic acid fibres have at least 95% of the acid residues in the unsalted form.

Suitable mono- or divalent cations of use in step (2) include solutions of sodium, potassium and magnesium cations. Preferably a pharmaceutically acceptable monovalent cation is used, most preferably a sodium ion.

Step (3) is preferably effected by washing the fibres in a stream of deionized water. Desirably step (3) may be discontinued when swelling has ceased.

Cations capable of forming water-soluble alginate salts include, for example, sodium, potassium, lithium, ammonium and magnesium cations. Preferably the source of a cation capable of forming a water-soluble alginate salt used in step (4) is a source of sodium cations, more preferably sodium carbonate. Other carbonates may be used in like manner to produce the alternative salts.

Small quantities of other ions (for example zinc or silver) may be present in step (4) if desired but generally these may be included in the fibre after completion of step (4) if their presence is required.

A method of treating the product of the above process to include other ions is to treat the product with an aqueous solution of a source of the ions.

The fibres may be collected at the end of step (4) by filtration or other suitable method and may be dried, for exmaple by treatment with acetone and then drying in air. It is one of the advantages of this invention that the highly absorbent fibres may be dried without losing their ability to be highly absorbent when rewetted.

The fibres may be treated with an aqueous solution of a desired ion, for example if it is desired to increase the calcium ion content treatment with a source of calcium ions such as a solution of calcium chloride may be used. In such treated fibres the higher of the two maxima (that generally found within the range 280–300° C.) tends to be reduced to a shoulder on the lower of the two maxima (that generally found with a maximum in the range of 200–250° C.). However, the skilled worker will appreciate that a shoulder represents a second peak and the two peaks may be separately drawn using standard computer aided calculations if desired.

For the most highly absorbent products to be obtained, large amounts of divalent ions such as calcium ions are not added at step (4) or later.

Aptly the fibres have a staple length of 0.25 to 25 mm, more usually 0.5 to 15 mm, favourably 1 to 12 mm and preferably 1.5 to 10 mm.

The alginate may be obtained from any convenient source, for example L. Hyperbola or Eclomia Maxima of which Eclonia Maxima is preferred.

The fibres prepared according to the abovedescribed process may be dried using conventional methods, for example, using acetone or hot air drying.

The solubility of the fibres may be modified by choosing the degree of neutralization of the unsalted carbonyl groups by solubilizing ion. Thus for example, if a sheet of fibres (such as may be employed in a dressing) is required which is highly absorbent but which will remain intact as gelled fibres, the fibres are produced under conditions where a small proportion of residual carboxy groups is retained (for example by using insufficient $Na_2CO_3$ or the like to effect complete neutralization). Alternatively, the material can be made fully soluble by replacing essentially all of the unsalted carboxy groups with a solubilizing ion such as sodium (for example by using at least a sufficient amount of $Na_2CO_3$ or the like to effect complete neutralisation).

A method of preparing fibres having a higher calcium content than those prepared directly by the process of the invention which employs sufficient $Na_2CO_3$ is to treat the fibre with calcium ions, for example from a solution of calcium chloride or the like, so that some of the sodium ions are replaced by calcium ions. Surprisingly the resulting mixed calcium/sodium salt has higher solubility than mixed calcium/sodium alginate fibres (of similar Ca:Na ratio) formed by conventional processes. The first order derivative of percentage weight loss of the fibre with temperature retains the two maxima in the range 200 to 300° C.

The present invention also provides fibres which have medicaments incorporated therein. This aspect of the invention is particularly relevant when the fibres are used in a dressing. Suitable medicaments include those which aid recovery of wounds, for example an antibacterial agent, an angiogenisis promoting agent or the like. Favoured medicaments include antibacterial agents such as chlorhexidine, for example a salt such as the acetate or glucoumate prepared by treating the fibres with an aqueous solution of the medicament or its salt.

It is one of the surprising advantages of the high absorbency fibres of this invention that they can be swollen, dried (for example with acetone) and rehydrated and still retain their high absorbency. This allows for ready sterilization, for example by drying, irradiating and rehydrating.

It has further been found that hyaluronic acid can be incorporated into fibres according to the present invention.

Hyaluronic acid (hereinafter referred to as HA) is a natural high viscosity mucopolysaccharide, generally having a molecular weight range of $3\times10^3$ to $8\times10^6$ Daltons (although there are reports of HA having molecular weights as high as $13\times10^6$) depending on source, method of isolation and method of determination. The isolation and characterisation of HA are described in Meyer, et al., J. Biol. Chem. 107, 629, (1934); J. Biol. Chem. 114, 689, (1936); Balazs, Fed. Proc. 17, 1086, (1958); Laurent, et al., Biochem. Biophys. Acta. 42, 476, (1960); Weissman, et al., J. Am. Chem. Soc., 76, 1753, (1954); and Meyer, Fed. Proc. 17, 1075, (1958).

HA is normally employed as its sodium salt although some other salting ions such as potassium or calcium or the like may also be preesnt. All such physiologically acceptable forms and especially the sodium salt are encompassed within the term HA herein.

HA is frequently used in ocular surgery as a replacement for subretinal fluid and vitreous humor. HA can also be used as a replacement for synovial fluid that is lost as a result of surgery or chronic inflammatory disease such as rheumatoid arthritis. HA is also known to be implicated in wound healing and angiogenesis. A wound dressing capable of providing sustained release of hyaluronic acid might therefore be expected to promote wound healing and/or angiogenesis.

There are accordingly further provided fibres in accordance with the present invention additionally comprising hyaluronic acid.

A suitable average molecular weight range for HA for use in the fibres of the present invention is $1.5\times10^3$ to $2\times10^6$, such as $1\times10^4$ to $1\times10^6$, preferably $1.5\times10^4$ to $1\times10^5$, more preferably about $7.5\times10^4$.

It is believed that the HA incorporated into fibres of the invention resides in spaces or "pockets" in the internal structure of the fibre and that release of the HA from the fibre to the environment of use takes place in a sustained manner as the fibre swells under the conditions of use. For example, fibres according to the present invention containing HA may be formed into a fabric used to prepare a wound dressing. As the dressing absorbs wound exudate, the fibres swell and HA is delivered to the wound in a sustained manner.

Incorporation of HA into the fibres of the invention may be achieved by contacting fibres according to the invention with an aqueous solution of HA followed by a suitable aqueous ionic solution, such as a solution of calcium, magnesium or zinc cations, preferably a solution of calcium cations, more preferably aqueous calcium chloride solution.

Alginate fabric prepared substantially entirely from fibres in accordance with the invention has considerably improved absorbency as compared to fabric prepared from conventional alginate fibres.

Figure 4:
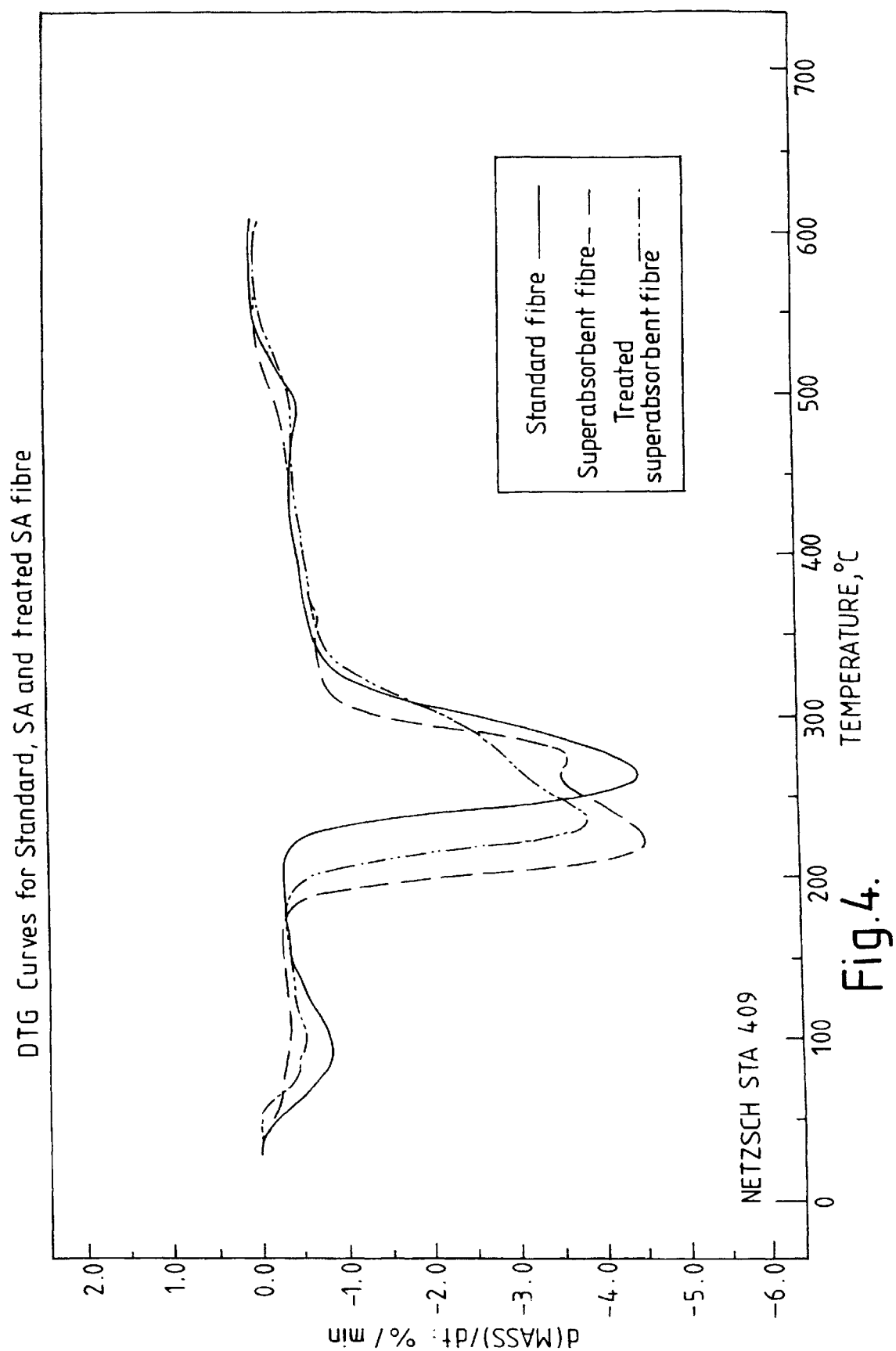
FIG. 4 shows the thermogravimetric analysis of a conventional fibre, a high absorbency fibre according to this invention and such a fibre treated with calcium ions.

The present invention accordingly provides an alginate fabric, characterized in that the absorbency of the fabric is at least 40.0 grams of deionized water per gram of fabric as measured with reference to the test method depicted in FIG. 4 appended hereto.

Fabric prepared substantially entirely from the fibres of the present invention has an absorbency of at least 40 times its own weight of deionized water and more aptly at least 60 times and most aptly at least 80 times its own weight of deionised water. Typically the fabric has an absorbency of much greater than this, for example 80 to 280 times its own weight, such as about 120 grams of deionised water per gram of fabric.

In a further aspect, the present invention provides an alginate fabric formed in whole or in part from the alginate fibres according to the invention.

In a particular embodinent, there is provided an alginate fabric formed in whole or in part from alginate fibres according to the invention, which fibres include hyaluronic acid.

In some circumstances it is desirable to produce fibres of relatively low absorbency which contains haluronic acid. Such fibres (with absorbency of 5–40 g of water per gram of haluronic acid containing fibres form an aspect of this invention. Similarly, dressings comprising fibres containing haluronic having said absorbency form an aspect of this invention. Such fibres are prepared by the process of hereinbefore described followed by treatment with a source of calcium ions, for example a solution of calcium chloride, which is sufficiently concentrated and for sufficient time to produce the desired solubility. Alginate fibres containing hyaluronic acid or its salts have not been produced by prior art methods.

The alginate fabric in accordance with the invention may, for example, be non-woven, woven or knitted and may be prepared by conventional methods. The fabric according to the invention may be embossed, for example by stitching or calendering regions of the fabric, so as to produce a fabric of increased structural integrity. The alginate fabric may consist essentially of alginate fibres of this invention or in part of such fibres. A favoured form of the fabric consists essentially of fibres of this invention.

The alginate fibres according to the invention may also be formed into a fabric using wet-laying techniques such as those conventional in the paper industry. Conventional alginate fibres cannot be wet-laid using conventional paper-making techniques. The ability of the fibres of the present invention to be wet-laid by conventional methods represents an important advantage of the inventive fibres over conventional alginate fibres.

In a preferred embodiment the present invention therefore provides an alginate fabric formed in whole or in part from alginate fibres in accordance with this invention prepared by wet-laying of the alginate fibres.

In a still further aspect, the present invention provides an alginate yarn formed in whole or in part from the alginate fibre according to the invention, optionally incorporating hyaluronic acid preferably as its sodium salt.

The alginate yarn according to the invention may be prepared by conventional methods.

The present invention further provides a wound dressing comprising an alginate fabric according to the invention.

The fabric in such dressings is typically 0.5 to 5 mm thick.

As used herein, the expression "wound dressing" includes surgical dressings. The term "wound" includes burn, scald, cut, sore, ulcer, blister, rash or any other lesion or area of troubled skin.

The wound dressings encompassed by the invention may comprise one or more of the wound dressing components well known in the art. For example, the wound dressing may comprise one or more adhesive layers. The wound dressing may also comprise one or more absorbent layers in addition to the alginate fibres of the invention. The wound dressing may also comprise a separate and discrete layer which faces the wound.

The dressings of the invention may also be advantageously adapted for use as burn dressings.

As used herein, the term "burn" includes burn, scald and the like.

In the management of burns, the affected site is desirably kept continually moistened, since it has been observed that an extremely effective treatment for burns is to allow cool water to penetrate over a prolonged period to the layers of skin underlying the affected area. It is accordingly envisaged that the burn dressing of the present invention would be applied in a wetted state, either with pure water or preferably with saline water; to the site of the burn. The high water retention capability of the dressing of the invention will ensure that an appreciable supply of water is available from the wetted burn dressing, to assist cooling by transpiration. A further advantage of the dressing of the invention is that it does not drip when applied to a curved surface such as an area of the human body, in contrast to conventional burn dressings such as surgical gauze and cotton wool which have a propensity to allow water to "run off".

The burn dressing of the invention may suitably be supplied in a pre-wetted state, or alternatively may be supplied in the dry state with instructions for wetting before application to the affected area in the eventuality of a burn. If supplied in a pre-wetted state, the burn dressing will advantageously incorporate conventional preservatives, for example Metasol D3T (Merck), Parasept (methyl paraben) (Kaloma Chemical) or Bromopol (2-bromo-2-nitro-1,3-propanediol) (Boots Ltd.), in order to prevent or retard the biological degradation of the fabric constituents.

The wound dressings formed from the alginate fabric according to the present invention will advantageously be conventional dressings well known in the art. Examples of suitable dressings include bandages, adhesive strip dressings, island dressings, pads of various kinds, surgical sponges and packs and ward dressings. Such dressings may conveniently be prepared by standard methods known from the art.

The dressings in accordance with the present invention will conveniently be packaged in an hermetically-sealed envelope and sterilised, e.g. with ethylene oxide or by irradiation using gamma rays or an electron beam.

The absorbency of fabric according to the invention may be determined according to the following method.

TEST METHOD

Figure 5:
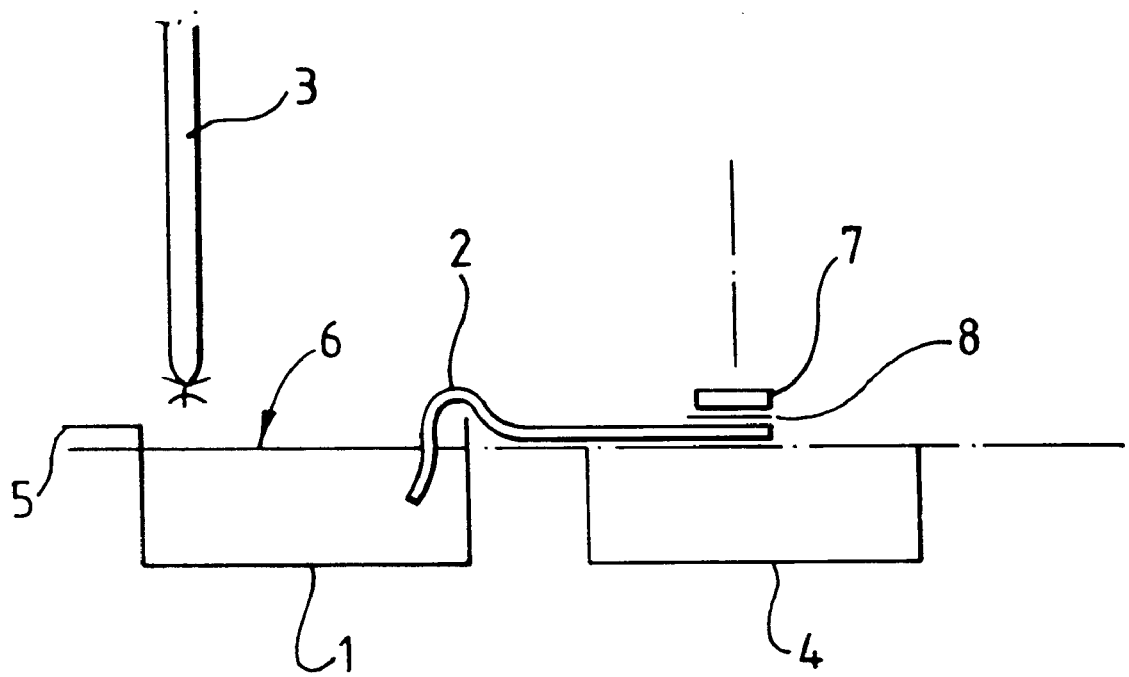
FIG. 5 shows apparatus suitable for determining absorbency.

The apparatus used in the determination of absorbency is depicted in FIG. 5, and consists of water bath 1 containing a 0.9% (w/w) aqueous saline solution, or deionised water, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7, but not necessarily the same thickness.

The apparatus is set up with the surface 6 of the saline solution or water level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 1. The balance 4 is then tared. A weighed dressing 7 and filter paper 8 (cut to size) is positioned as depicted in FIG. 4. Care must be taken to ensure that the edge of the absorbent strip 2 furthest away from the water bath 1 does not extend beyond the corresponding edge of the dressing 7, as shown in FIG. 4.

After six minutes the weight shown on the balance 4 is recorded. The dressing 7 and filter paper 8 are then removed and any residual weight on the balance 4 noted.

Absorbency is determined on the basis of the following equation:

$$\begin{array}{c}\text{wt. of liquid}\\ \text{absorbed}\end{array} = \begin{array}{c}\text{total wt.}\\ \text{on balance}\end{array} - \begin{array}{c}\text{dry wt.}\\ \text{dressing}\end{array} + \begin{array}{c}\text{wt. of satd.}\\ \text{filter paper}\end{array} + \begin{array}{c}\text{residual wt.}\\ \text{on balance}\end{array}$$

The following non-limiting Examples are intended to illustrate the present invention.

EXAMPLE 1

Calcium alginate fibre (4 g) was immersed in 1M hydrochloric acid (1 l) for 20–30 seconds. The degree of acid conversion was determined from the relative intensities of the peaks at 1720 cm$^{-1}$ and 1600 cm$^{-1}$ in the infrared spectrum, to ensure that the degree of conversion was in excess of 95%. The fibre was then washed with water and immersed in saturated saline solution (2 l). The fibre was then chopped to the required staple length. After cutting to the appropriate length the fibre was dispersed into a stirred vessel containing deionised water (2 l). The fibres were washed in a stream of running water until they swelled to their maximum extent and no sodium chloride could be detected in the eluent. Sodium carbonate solution (0.1M) was then added in 1 ml aliquots whilst monitoring the pH and conductivity of the medium. Care was taken to ensure that the pH did not exceed 6.5. After the addition of approximately 12 mls of sodium carbonate solution (conductivity meter reading between 180 and 200 micro siemens), the material was filtered and dried with acetone followed by air drying.

EXAMPLE 2

Fibres prepared as described in Example 1 (5 g) were added slowly with vigorous stirring to a solution prepared by dissolving sodium hyaluronate (av. mol. wt. 7.5×10$^4$ 1 g) in deionised water (100 ml). Acetone (30 ml) was added to the slurry, followed by aqueous calcium chloride solution (20 ml, 0.2M). The fibres were isolated by filtration, washed with acetone (200 ml) and air dried.

EXAMPLE 3

A pad of fibres prepared as described in Example 1 (1 g) was cut to size and placed in a Buchner funnel such that the bottom surface of the funnel was completely covered. A solution of sodium hyaluronate (av. mol. 7.4×10$^4$, 0.1 g) in deionised water (10 ml) was carefully poured onto the pad of fibres. Suction was applied to remove excess water. An aqueous solution of calcium chloride (10 ml, 0.2M) was filtered through the fibre pad, followed by acetone (100 ml). The fibre pad was air dried.

EXAMPLE 4

Fibres prepared as dsecribed in Example 1 (5 g) were added slowly with vigorous stirring to deionized water (100 ml). Acetone (30 ml) was added to the slurry the fibres were isolated by filtration, washed with acetone (200 ml) and air dried. The resulting 1 mm thick pad was trimmed to 5×5 cm and was placed in a bacteria proof pouch which was sealed and sterilized by irradiation (for example by gamma irradiation).

We claim:

1. Alginate fabric which absorbs at least 40.0 g of deionized water per gram of fabric and 80 to 280 times its own weight of deionized water.

2. Alginate fabric as claimed in claim 1 which comprises a febre characterized in that a plot of the first order derivative of percentage weight loss of the fibre with temperature against temperature has two maxima in the range 100° to 400° C.

3. Alginate fabric as claimed in claim 2 in which the plot of the first order derivative of percentage weight loss of the fibre with temperature against temperature has two maxima in the range 200° to 300° C.

4. Alginate fabric as claimed in claim 1 which comprises a fibre characterized in that its glass transition range is less than 30° C.

5. Alginate fabric as claimed in claim 1 which comprises a fibre which absorbs at least 40.0 g deionized water per gram of fibre.

6. A process for the preparation of alginate fibres to prepare alginate fabric as claimed in claim 1 which comprises the following steps:

(1) treating alginate fibres with a suitable acid so as to produce fibres comprising approximately 90–98% alginic acid fibres;

(2) treating the alginic acid fibres with a saturated aqueous solution of mono- or divalent cations;

(3) washing the fibres with water until imbibition of water by the fibres has effectively ceased; and (4) treating the fibres with a source of a cation capable of forming a water-soluble alginate salt.

7. A process as claimed in claim 6 wherein the alginate fibres in step 1 are calcium alginate.

8. A process as claimed in claim 7 wherein the acid used in step (1) is hydrochloric acid.

9. A process as claimed in any of claims 6 to 8 wherein the solution used in step (2) is a solution of sodium ions.

10. A process as claimed in any of claims 6 to 8 wherein step (3) comprises washing in deionized water.

11. A process as claimed in any of claims 6 to 8 wherein other ions and/or medicaments are included after or during step 4.

12. Alginate fabric as claimed in claim 1 which comprises a fibre characterized in that a plot of the first order derivative of percentage weight loss of the fibre with temperature against temperature has two maxima in the range 100° to 400° C. and which contains the sodium salt of hyaluronic acid.

13. A dressing which comprises a fibre or fabric as claimed in any of claims 1 or 2 to 5.

14. A dressing as claimed in claim 13 in the form of a sterile dressing for the treatment of a burn or ulcer or other exuding wound.

15. A process as claimed in claim 6 wherein the alginate fibres in step (1) are treated with a suitable acid so as to produce fibres comprising approximately 95–98% alginic acid fibres.

16. Alginate fabric as claimed in claim 1 which comprises a fibre characterized in that its glass transition range is less than 30° C. and which contains the sodium salt of hyaluronic acid.

17. Alginate fabric as claimed in claim 1 which comprises a fibre which absorbs at least 40.0 g deionized water per gram of fibre and which contains the sodium salt of hyaluronic acid.

18. A fabric as claimed in claim 1, 2, 5, 12, 16 or 17 which is a wet layered fabric.

* * * * *